United States Patent
Karinaga et al.

(10) Patent No.: US 10,837,011 B2
(45) Date of Patent: Nov. 17, 2020

(54) METHOD AND REAGENT FOR EXTRACTING NUCLEIC ACID

(71) Applicant: UNIVERSAL BIO RESEARCH CO., LTD., Matsudo-shi, Chiba (JP)

(72) Inventors: Ryouji Karinaga, Matsudo (JP); Tetsuya Ueda, Matsudo (JP); Hideji Tajima, Matsudo (JP)

(73) Assignee: UNIVERSAL BIO RESEARCH CO., LTD., Matsudo (JP)

( * ) Notice: Subject to any disclaimer, the term of this patent is extended or adjusted under 35 U.S.C. 154(b) by 251 days.

(21) Appl. No.: 15/123,582

(22) PCT Filed: Mar. 18, 2015

(86) PCT No.: PCT/JP2015/058009
§ 371 (c)(1),
(2) Date: Sep. 2, 2016

(87) PCT Pub. No.: WO2015/146737
PCT Pub. Date: Oct. 1, 2015

(65) Prior Publication Data
US 2017/0081656 A1    Mar. 23, 2017

(30) Foreign Application Priority Data
Mar. 26, 2014  (JP) ................ 2014-063407

(51) Int. Cl.
*C12N 15/10* (2006.01)

(52) U.S. Cl.
CPC ..... *C12N 15/1013* (2013.01); *C12N 15/1006* (2013.01)

(58) Field of Classification Search
None
See application file for complete search history.

(56) References Cited

U.S. PATENT DOCUMENTS

| | | | |
|---|---|---|---|
| 5,234,809 A * | 8/1993 | Boom | C07H 21/00 422/504 |
| 5,681,946 A * | 10/1997 | Reeve | B03C 1/01 252/62.54 |
| 6,043,032 A * | 3/2000 | Yamagishi | C12N 15/1003 435/270 |
| 6,582,922 B1 | 6/2003 | Daimon et al. | |
| 2007/0244314 A1 * | 10/2007 | Mori | C12N 15/1006 536/25.41 |
| 2009/0048439 A1 * | 2/2009 | Weisburg | C12N 15/1006 536/25.41 |
| 2009/0176296 A1 * | 7/2009 | Skagestad | C12N 15/1006 435/274 |
| 2010/0291666 A1 * | 11/2010 | Collier | B01L 3/502715 435/287.2 |
| 2012/0122753 A1 | 5/2012 | Schmiedel et al. | |
| 2012/0309104 A1 | 12/2012 | Uematsu et al. | |

FOREIGN PATENT DOCUMENTS

| | | | | |
|---|---|---|---|---|
| EP | 0389063 A2 * | 9/1990 | | C07H 21/00 |
| EP | 1 873 241 A1 | 1/2008 | | |
| JP | 7-59572 A | 3/1995 | | |
| JP | 9-327291 A | 12/1997 | | |
| JP | 2006-6258 A | 1/2006 | | |
| JP | 2012-223098 A | 11/2012 | | |
| WO | WO 2005/089929 A2 | 9/2005 | | |
| WO | WO2005089929 * | 9/2005 | | B01J 19/00 |
| WO | WO 2011/074456 A1 | 6/2011 | | |
| WO | WO 2012/069660 A1 | 5/2012 | | |

OTHER PUBLICATIONS

Berensmeier S. Magnetic particles for the separation and purification of nucleic acids. Appl Microbiol Biotechnol. Dec. 2006; 73(3): 495-504. Epub Oct. 25, 2006. (Year: 2006).*
International Search Report issued in PCT/JP2015/058009, dated Jun. 2, 2015.
Written Opinion of the International Searching Authority issued in PCT/JP2015/058009 (PCT/ISA/237), dated Jun. 2, 2015.
English translation of International Preliminary Report on Patentability and Written Opinion dated Oct. 6, 2016, in PCT International Application No. PCT/JP2015/058009.
Extended European Search Report dated Oct. 2, 2017, in European Patent Application No. 15769685.7.

* cited by examiner

*Primary Examiner* — Teresa E Strzelecka
*Assistant Examiner* — Olayinka A Oyeyemi
(74) *Attorney, Agent, or Firm* — Birch, Stewart, Kolasch & Birch, LLP

(57) ABSTRACT

In a method of nucleic acid extraction using a support, the present invention realizes collection of a nucleic acid from a liquid containing the nucleic acid at an extremely low concentration at which collection cannot be achieved with polyacrylamide.
A method of extracting a nucleic acid, comprising allowing the nucleic acid to be adsorbed onto a support in the presence of a chaotropic salt and an alcohol in coexistence with an anionic polymer. A reagent for nucleic acid extraction, comprising an anionic polymer, a chaotropic salt, an alcohol and a support.

9 Claims, 2 Drawing Sheets
Specification includes a Sequence Listing.

ved by allowing an anionic polymer (which is a non-biological material) to coexist with a target nucleic acid. Thus, the present invention has been achieved.

METHOD AND REAGENT FOR EXTRACTING NUCLEIC ACID

TECHNICAL FIELD

The present invention relates to a method and a reagent for nucleic acid extraction. More specifically, the present invention relates to a method of nucleic acid extraction using a support as well as a reagent therefor.

BACKGROUND ART

Recently, genetic examination is applied diversely to, for example, tests to identify viruses or pathogenic bacteria, detection of pathogenic microorganisms at an early stage of infection, survey of the source of infection, and even diagnosis of leukemia or tumor at the genetic level. Among all, detection of the nucleic acid of pathogenic microorganisms for the purpose of diagnosis of infection is one of a few techniques for early detection of infection and confirmation of progress after treatment. For this purpose, it is necessary to extract and collect target nucleic acids at very low concentrations from samples such as body fluids.

Sometimes, a carrier is used for extracting and collecting a trace nucleic acid from samples. As a carrier, a nucleic acid or a substance having a chemical property similar to that of nucleic acid (in terms electric charge, molecular size, etc.) is used. Specifically, nucleic acid carriers such as poly(A), poly(dIdC) or tRNA, or biopolymer carriers such as glycogen are known (Non-Patent Documents Nos. 1 and 2). When a biomolecule is used as a carrier, it is apprehended that a natural nucleic acid which potentially affects the detection of a target nucleic acid might be mixed in the subsequent step. Therefore, it is desirable that the carrier is not a biomolecule.

Further, a method has been reported recently in which a nucleic acid is extracted using its ability to bind to a support such as silica (Non-Patent Document No. 3).

PRIOR ART LITERATURE

Non-Patent Documents

Non-Patent Document No. 1: Gaillard, C. and Strauss, F., Nucleic Acid Research, Vol. 18, 378 (1990)
Non-Patent Document No. 2: Sambrook, J. and Russell, D. W., Molecular Cloning: A Laboratory Manual, 3rd ed., A8.12 (2001)
Non-Patent Document No. 3: B. Vogelstein and D. Gillespie, Proc. Natl. Acad. Sci. USA, 76(2), 615-619 (1979)

DISCLOSURE OF THE INVENTION

Problem to be Solved by the Invention

Although polyacrylamide is known as anon-biological material carrier, polyacrylamide is used not in techniques of binding a nucleic acid to a support but in techniques such as ethanol precipitation that use a centrifuge. It is an object of the present invention to realize, in a method of nucleic acid extraction using a support, collection of a nucleic acid from a liquid containing the nucleic acid at an extremely low concentration at which collection cannot be achieved with polyacrylamide.

Means to Solve the Problem

As a result of intensive and extensive researches, the present inventors have found that it is possible to improve the amount of nucleic acid collection by allowing an anionic polymer (which is a non-biological material) to coexist with a target nucleic acid. Thus, the present invention has been achieved.

A summary of the present invention is as described below.

[1] A method of extracting a nucleic acid, comprising allowing the nucleic acid to be adsorbed onto a support in the presence of a chaotropic salt and an alcohol in coexistence with an anionic polymer.

[2] The method of [1], wherein the anionic polymer is a polymer having a carboxyl group in its side chain.

[3] The method of [1], wherein the anionic polymer is at least one polymer selected from the group consisting of polyacrylic acid, polyacrylates, polyacrylic acid derivatives, copolymers comprising polyacrylic acid, polyacrylamide derivatives having a carboxyl group, polysilane derivatives, carboxymethyl cellulose, carboxymethyl cellulose salts, polyglutamic acid, polyglutamates, polyglutamic acid derivatives and copolymers comprising polyglutamic acid.

[4] The method of [1], wherein the alcohol is at least one alcohol selected from the group consisting of ethanol, isopropyl alcohol, n-propanol, n-butanol and 2-butanol.

[5] The method of [1], wherein the chaotropic salt is at least one chaotropic salt selected from the group consisting of guanidine hydrochloride, guanidine thiocyanate salt (guanidine thiocyanate), guanidine sulfate, guanidine isothiocyanate, sodium isocyanate, sodium iodide, potassium iodide, urea, sodium bromide, potassium bromide, calcium bromide, ammonium bromide, sodium perchlorate, sodium thiocyanate, potassium thiocyanate, ammonium isothiocyanate, sodium chloride, potassium chloride and ammonium chloride.

[6] The method of [1], wherein the support is a solid having a hydrophilic functional group in its surface layer.

[7] The method of [6], wherein the hydrophilic functional group is at least one functional group selected from the group consisting of hydroxyl group, carboxyl group, carbonyl group, nitro group and silanol group.

[8] The method of [6], wherein the support is magnetic particles.

[9] The method of any one of [1] to [8], which is regulated in an automated device.

[10] The method of [9], wherein the support is magnetic particles; suspension of the magnetic particles is handled with a disposable chip; and solid-liquid separation is carried out by capturing the magnetic particles on the inner wall surface of the chip with a magnet being applied to the outer wall surface of the chip.

[11] A reagent for nucleic acid extraction, comprising an anionic polymer, a chaotropic salt, an alcohol and a support.

[12] The reagent of [11], which further comprises a buffer.

[13] The reagent of [11] or [12], which is contained in a kit to be enclosed in a cartridge.

Effect of the Invention

Anionic polymers enhance the effect of binding of nucleic acids to supports. According to the present invention, it has become possible to collect a target nucleic acid from liquids containing the nucleic acid at an extremely low concentration.

The present specification encompasses the contents disclosed in the specification and/or the drawings of Japanese Patent Application No. 2014-063407 based on which the present patent application claims priority.

BEST MODES FOR CARRYING OUT THE INVENTION

Figure 1:
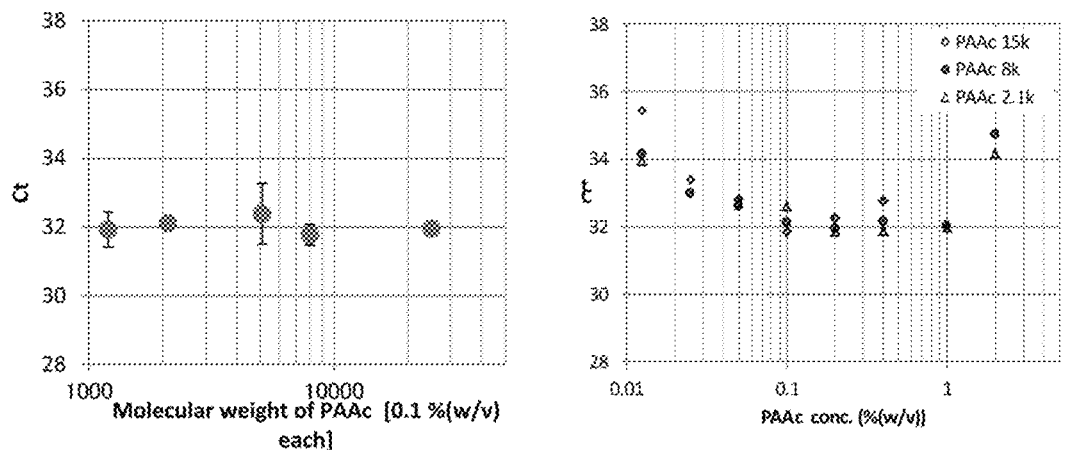
FIG. 1 Left Panel: Dependency of carrier effect on the molecular weight of polyacrylic acid (PAAc) (0.1% (w/v) for each). When distilled water (DW) was used instead of a carrier, no Ct values could be obtained. Right Panel: Dependency of carrier effect on PAAc concentration.

Hereinbelow, embodiments of the present invention will be described in detail.

The present invention provides a method of nucleic acid extraction, comprising allowing the nucleic acid to be adsorbed onto a support in the presence of a chaotropic salt and an alcohol in coexistence with an anionic polymer.

The nucleic acid may be any one of double-stranded DNA, single-stranded DNA or RNA and may be either a natural nucleic acid derived from biological tissues, cells, viruses, etc. or a synthetic nucleic acid. Specific examples of "solution containing a nucleic acid" include, but are not limited to, a part of a biological tissue or a crushed product thereof, body fluids [e.g., blood (whole blood, serum, plasma or the like), urine, saliva, amniotic fluid, breast milk, spinal fluid, synovial fluid, peritoneal fluid, pleural fluid, aural discharge, nasal discharge, pus, bile, sputum, sweat or the like], solutions containing a lysed sample of mucosa, stool, cell or the like, plants, liquids treated with enzymes, and PCR products.

The method of the present invention makes it possible to extract and collect a nucleic acid from a liquid containing the nucleic acid at an extremely low concentration.

The anionic polymer may be a polymer which is negatively charged in aqueous solutions. Further, the anionic polymer may be a polymer which does not inhibit detection and quantification of the target nucleic acid performed after the nucleic acid extraction step, and may be a polymer which does not agglutinate the support in the nucleic acid extraction step. As the anionic polymer, a polymer having a carboxyl group in its side chain is preferable; and such a polymer may be a water-soluble polymer.

Specific examples of the anionic polymer include, but are not limited to, polyacrylic acid, polyacrylates (sodium polyacrylate, potassium polyacrylate, calcium polyacrylate, etc.), polyacrylic acid derivatives (ethyl polyacrylate, polyacrylic acid esters, etc.), copolymers containing polyacrylic acid (copolymers of acrylic acid and maleic acid, styrene-acrylic acid copolymers, ethylene-acrylic acid copolymers, polyoxyethylene-polyacrylic acid copolymers, etc.), polyacrylamide derivatives having a carboxyl group (polyacrylamide-polyacrylic acid copolymers, etc.), polysilane derivatives (polycarbosilane, polyphenylsilane, etc.), carboxymethyl cellulose, carboxymethyl cellulose salts (carboxymethyl cellulose sodium, carboxymethyl cellulose potassium, carboxymethyl cellulose calcium, etc.), polyglutamic acid, polyglutamates (sodium polyglutamate, potassium polyglutamate, calcium polyglutamate, etc.), polyglutamic acid derivatives (polyglutamic acid esters, benzyl polyglutamate, etc.), copolymers containing polyglutamic acid (polyoxyethylene-polyglutamic acid copolymers, polystyrene-polyglutamic acid copolymers, etc.) and combinations thereof.

The amount of addition (concentration) of the anionic copolymer is not particularly limited. For example, when the anionic copolymer is polyacrylic acid, 0.02-0.2% (v/v) as the final concentration of the carrier in the reaction solution is appropriate. Preferably, the concentration is 0.02-0.1% (v/v).

The support may be any support as long as it is capable of adsorbing nucleic acids. The material thereof is not particularly limited, but preferably the support is a solid having a hydrophilic functional group in its surface layer. Specific example of the hydrophilic functional group include, but are not limited to, hydroxyl group, carboxyl group, carbonyl group, nitro group and silanol group. It is possible to give a hydrophilic functional group to a support by treating its surface. For example, silica coating will give a silanol group to the surface of a support.

When the support assumes a core-coated structure as one embodiment, the core component may be any one of a metal oxide (silica, alumina, ferrite, magnetite, etc.) or a polymer (polystyrene, acrylic resin, cellulose, dextran, etc.) and the coating component may be any one of a metal oxide (silica, alumina, etc.), a polymer (cellulose, dextran, poly acrylic acid, etc.) or a coupling agent (silane-based, titanate-based, aluminate-based, etc.). The coating component and the core component may be the same.

The support may assume any shape, such as sheet, sieve, membrane, amorphous particles, spheres (beads), yarn (strand), magnetic beads, etc. Preferably, the shape of the support is spherical. It is preferred that the support is magnetic particles.

Spheres (beads) may be about 1 mm in size, and the material thereof may be plastic, ceramic or the like. Such spheres (beads) are disclosed in, for example, Japanese Unexamined Patent Publication No. 2000-346842 and Japanese Unexamined Patent Publication (Translation of PCT Application) No. 2002-534657.

Magnetic beads may be several ten μm in size and prepared by mixing iron powder or the like with plastic, ceramic, etc. for magnetization. Such magnetic beads are disclosed in, for example, Japanese Unexamined Patent Publication No. 1996-62224 (Japanese Patent No. 3115501), WO96/29602 and WO97/44671.

Yarn (strand) may be about 0.1 mm in diameter and made from a resin-type material. Such a yarn is disclosed in, for example, Japanese Unexamined Patent Publication No. 2006-214759, WO01/53831 and WO2003/7901.

Nucleic acids are capable of being adsorbed onto supports by means of covalent bonding, chemical adsorption, physical adsorption, electric interaction, hydrophobic interaction, van der Waals force, hydrogen bonding or the like.

It is possible to allow nucleic acids to be adsorbed onto supports by insolubilizing the nucleic acid with chaotropic salts and alcohols.

An alcohol which is capable of insolubilizing nucleic acids may be used. Specific examples of the alcohol include, but are not limited to, ethanol, isopropyl alcohol, n-propanol, n-butanol, 2-butanol and combinations thereof.

Specific examples of chaotropic salts include, but are not limited to, guanidine hydrochloride, guanidine thiocyanate salt (guanidine thiocyanate), guanidine sulfate, guanidine isothiocyanate, sodium isocyanate, sodium iodide, potassium iodide, urea, sodium bromide, potassium bromide, calcium bromide, ammonium bromide, sodium perchlorate, sodium thiocyanate, potassium thiocyanate, ammonium isothiocyanate, sodium chloride, potassium chloride, ammonium chloride and combinations thereof.

The nucleic acid adsorbed onto the support may be washed and then eluted into an eluent for collection. By detecting and quantifying the thus collected nucleic acid, it is possible to perform diverse genetic examinations such as tests to identify viruses or pathogenic bacteria, detection of pathogenic microorganisms at an early stage of infection, survey of the source of infection, and diagnosis of leukemia or tumor at the genetic level.

The nucleic acid extraction method of the present invention may be used as regulated in an automated device. Magtration™ System 6GC, 12GC and 12GC-PLUS (Precision System Science) are commercially available and may be used as fully automated nucleic acid extraction devices. Magtration is a coined word in a contracted form of "magnetic filtration" meaning sieving with a magnet and refers to a technique developed for automating the reaction of magnetic particles (and called a magnetic particle handling technique). Suspension of magnetic particles is handled with a disposable chip. It is possible to carry out solid-liquid separation by capturing the magnetic particles on the inner wall surface of the chip with a magnet being applied to the outer wall surface of the chip.

The present invention also provides a reagent for nucleic acid extraction, comprising an anionic polymer, a chaotropic salt, an alcohol and a support.

The anionic polymer, the chaotropic salt, the alcohol and the support are as defined above.

The reagent for nucleic acid extraction of the present invention may further comprise a buffer. Specific examples of the buffer include, but are not limited to, Tris-HCl, TE (Tris-HCl, EDTA) and phosphate buffer.

The reagent for nucleic acid extraction of the present invention may further comprise proteolytic enzymes (e.g., Proteinase K), surfactants (e.g., sodium dodecyl sulfate), water, antibiotics (e.g., ProClin 300), sodium azide or the like. These components may be contained in one or more wells as a single component or a mixture to thereby prepare a pre-pack reagent. Such a pre-pack reagent may further be combined with other consumables (e.g., chip, chip holder, screw cap tube, etc.) to thereby prepare a reagent kit.

The pre-pack reagent may be set in an automated device and mixed with a sample automatically. There may be included an automated step in which a support containing magnetic particles is separated from a liquid using an automated device equipped with a magnet.

Further, the reagent of the present invention may be prepared as a kit to be enclosed in a cartridge.

Hereinbelow, the present invention will be described in more detail with reference to the following Examples. However, the scope of the present invention is not limited to these Examples.

EXAMPLES

Example 1

Summary

The present inventors have found that poly(acrylic acid) (hereinafter, referred to as PAAc) is useful as a more effective carrier for collecting viral nucleic acid from serum or physiological saline.

Nucleic acid extraction step is carried out by the following procedures. (1) Samples containing a nucleic acid are treated with a lysis solution containing a guanidine salt. (2) The treated samples are mixed with a binding buffer containing an alcohol and a support having a hydroxyl group, a carboxyl group or silica on its surface layer, whereupon the nucleic acid is bound to the support. (3) The support is separated from the liquid components and obtained on its own. (4) The support is washed with a buffer containing 2-propanol. (5) The support is separated from the liquid components and obtained on its own. (6) The support is mixed with an eluent (distilled water or Tris-HCl) to recover the nucleic acid in the eluent (hereinafter, referred to as "collected nucleic acid solution").

The carrier, which is added in the above-described step (2), improves nucleic acid collection efficiency through its function of assisting and promoting the binding of the nucleic acid to the support.

The nucleic acid extraction step was performed with Magtration System 12GC PLUS
(Precision System Science).

Experimental Methods/Procedures (Evaluation of Carriers)

Two hundred copies/μl of M13 (a bacteriophage that infects *Escherichia coli*) was added in an amount of 20 μl to Consera (control serum; Nissui Pharmaceutical) (180 μl) and physiological saline (180 μl), separately. From the resultant samples each containing 20 copies/μl of M13, collection liquids were obtained by the above-described nucleic acid extraction step. In the process, a carrier (0.1% (w/v)) was added in the nucleic acid extraction step (2). The resultant individual collected nucleic acid solutions were subjected to real time PCR under the PCR conditions described below to thereby obtain Ct values. As a control, nucleic acid extraction was carried out using distilled water (DW) instead of the carrier. (Real Time PCR of M13 DNA)

The above-described nucleic acid extraction operations were performed using 200 μl of a sample solution of virus added to Consera or physiological saline. For each of the resultant collected nucleic acid solutions, real time PCR was performed under the conditions described below to thereby obtain Ct values and Tm. As a template, extracted M13KO7 DNA or M13KO7 was used.

Real time PCR reagent SsoAdvanced SYBR Green SuperMix (BIORAD, 172-5261) was used. The following primers were used: Forward Primer M13KO7-F 4984: 5'-GCTATCAGTTCGCGCATTAAAGAC-3' (SEQ ID NO: 1) (eurofins operon) and Reverse Primer M13KO7-R 5110: 5'-CATTGGCAGATTCACCAGTCACA-3' (SEQ ID NO: 2) (eurofins operon). As thermal cyclers, Applied Biosystems 7500 Fast real time PCR system: Life technologies and Thermal Cycler Dice Real Time System: TaKaRa TP800 S/N R-1387 were used. Reagent preparation for and temperature control during PCR were set as described below. For threshold, automatic setting was used.

| [PCR condition] | |
|---|---|
| SsoAdvanced SYBR Green SuperMix | 10 μl |
| M13KO7-F 4984 (50 μM) | 0.1 μl |
| M13KO7-R 5110 (50 μM) | 0.1 μl |
| dH$_2$O | 7.8 μl |
| Template | 2 μl |
| | 20 μl |

[Temperature control]

| | | |
|---|---|---|
| 95° C. | 30 sec. | |
| 95° C. | 5 sec. | } 45 Cycle |
| 60° C. | 30 sec. | |
| 95° C. | 15 sec. | |
| 60° C. | 15 sec. | |
| 95° C. | 15 sec. | |

(PAAc Molecular Weight Distribution and Concentration)

PAAc's with mean molecular weights of 25000, 15000, 8000, 5100, 2100 and 1200 (Sigma-Aldrich, 16-1858, 416037, 416029, 81132 and 81130) were dissolved with ProClin 300 (Sigma-Aldrich, 48912-U) (final concentration 1/2000) and 10 mM Tris-HCl (pH 7.5) to give a concentration of 0.1% (w/v). Using the resultant PAAc solutions, nucleic acid extraction operations were carried out. The resultant collected nucleic acid solutions were subjected to real time PCR under the PCR conditions described above to thereby obtain Ct values.

PAAc's with mean molecular weights of 15000, 8000 and 2100 were dissolved with ProClin 300 (final concentration 1/2000) and 10 mM Tris-HCl (pH 7.5) to give concentrations of 2, 1, 0.4, 0.2, 0.1, 0.05, 0.025 and 0.0125% (w/v). Using the resultant PAAc solutions, nucleic acid extraction operations were carried out. The resultant collected nucleic acid solutions were subjected to real time PCR under the PCR conditions described above to thereby obtain Ct values.

[Results and Discussion]

(PAAc Molecular Weight Distribution and Concentration)

With respect to PAAc molecular weight, PAAc's with mean molecular weights of 1.2 k, 2.1 k, 5.1 k, 8 k, 15 k and 25 k were dissolved with 10 mM Tris HCl (pH 7.5) and ProClin 300 (final concentration 0.05% (×2,000)) to give a concentration of 0.1% (w/v), and their effect as a carrier was confirmed by collection of M13 (20 copies/μl) spiked in physiological saline. As shown in the left panel of FIG. 1, no molecular weight dependency was observed between molecular weights 1200 and 25000. It can be said that PAAc exhibited the carrier effect at any of the molecular weights. When DW was used instead of the carrier, no Ct values could be obtained.

Further, dependency on concentration was evaluated using PAAc's with molecular weights of 2.1 k, 8 k and 15 k. As a result, any of the PAAc's exhibited the carrier effect at 0.1-1% (w/v) (FIG. 1, right panel). At PAAc concentrations of 0.5% (w/v) and below, Ct values improved with decreasing PAAc concentration. At 2% (w/v), Ct value increased by 2-3 compared to the values for the range of 0.1-1% (w/v) in which the highest carrier effect was obtained.

Example 2

Using polymers with skeletons resembling that of sodium polyacrylate and polymers having characters different from that of sodium polyacrylate, their effects as a nucleic acid carrier in nucleic acid extraction were evaluated.

[Experimental Methods and Procedures]

Individual polymers as listed in Table 1 were dissolved in distilled water to give a concentration of 0.15% (w/v) and used instead of PAAc to carry out nucleic acid extraction operations in the same manner as described in Example 1.

TABLE 1

Polymer List

| # | Name | Supplier | Code |
|---|---|---|---|
| 1 | Poly(acrylic acid, sodium salt) solution | ALDRICH | 416029 |
| 2 | Gelatin | Wako | 077-03155 |
| 3 | Hydroxy ethyl cellulose | Wako | 085-01935 |
| 4 | Poly vinyl alcohol | SIGMA-ALDRICH | P8136-250G |
| 5 | Poly ethylen imine solution | SIGMA-ALDRICH | P3143-100ML |
| 6 | Poly vinyl acetate | ALDRICH | 430439-25G |
| 7 | Poly ethylene glycol 20000 | Wako | 168-11285 |
| 8 | Poly ethylene-co-ethyl acrylate-co-maleic anhydride | ALDRICH | 43084-6 |
| 9 | Poly vinyl pyrrolidone | SIGMA-ALDRICH | 9003-39-8 |
| 10 | Poly-L-Lysine solution | SIGMA-ALDRICH | P8920 |
| 11 | Poly phosphoric acid | SIGMA-ALDRICH | 208213-25G |
| 12 | Carboxy methyl cellulose sodium salt | ALDRICH | 419173-100G |
| 13 | Dextran | Wako | 101507 |
| 14 | Poly(acrylic acid-co-maleic acid) solution | ALDRICH | 416053-250ML |
| 15 | Poly-L-glutamic acid sodium salt | SIGMA-ALDRICH | P1818-25MG |
| 16 | Polymaron 1318 | Arakawa Chemical Industries | sample |
| 17 | Polymaron 1343s | Arakawa Chemical Industries | sample |

Real time PCR of M13 DNA was performed in the same manner as described in Example 1 except in the following points. Physiological saline (200 μl) was used as a sample; $2 \times 10^3$ cp/μl of M13KO7 (10 μl) was added to a lysis solution, followed by nucleic acid extraction operations. Reagent preparation for PCR was as described below (Threshold was set at 100,000.).

[PCR condition]

| | |
|---|---|
| SsoAdvanced SYBR Green SuperMix | 15 μl |
| M13KO7-F 4984 (50 μM) | 0.15 μl |
| M13KO7-R 5110 (50 μM) | 0.15 μl |
| dH$_2$O | 4.7 μl |
| Template | 10 μl |
| | 30 μl |

[Results and Discussion]

Figure 2:
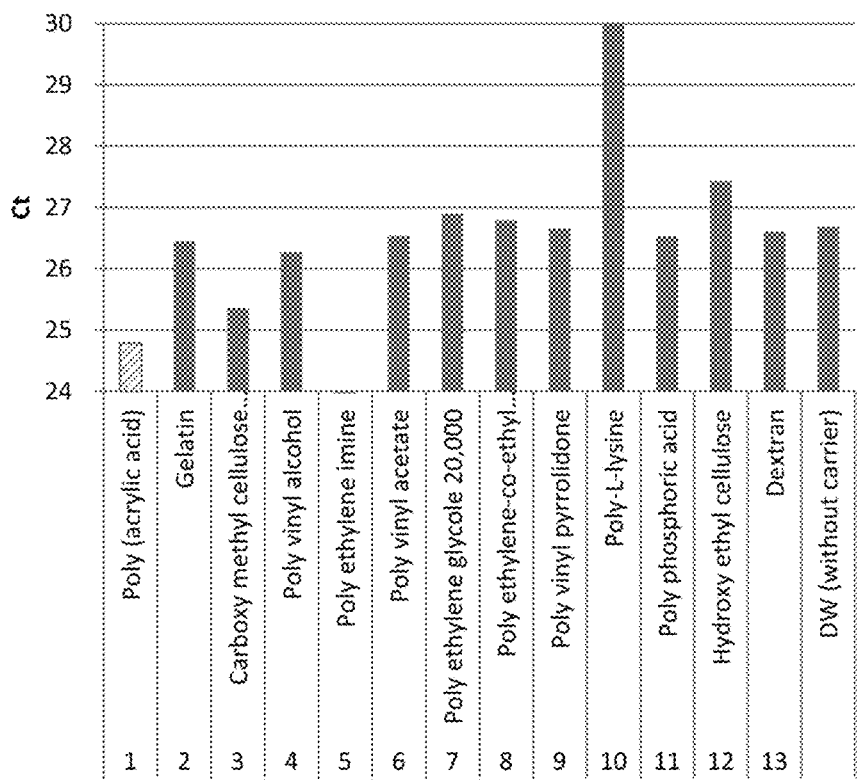
FIG. 2 Carrier effects of individual polymers 1.

Nucleic acid extraction was performed using 13 polymers including poly(acrylic acid sodium salt) instead of poly (acrylic acid) Ct values were obtained from real time PCR (Table 2, FIG. 2). Differences between Ct values obtained from using polymers and Ct values obtained from nucleic acid extraction without using carriers (Ct without carrier) were calculated. Carrier effect was evaluated as follows. When the difference is −1.0 or less, carrier effect is +; when the difference is −1.0 to −0.5, carrier effect is +w; when the difference is −0.5 to +0.5, carrier effect is ±; and when the difference is +0.5 or more, carrier effect is −.

As shown in Table 2, the carrier effects of poly(acrylic acid sodium salt) and carboxymethyl cellulose sodium salt, each having —COOH as a functional group, were rated +; high carrier effects were obtained. Polyethyleneimine and poly-L-lysine, each having many amino groups and being positively charged in aqueous solutions, inhibited nucleic acid collection. Polymers having other skeletons had no substantial effects on nucleic acid collection.

Figure 3:
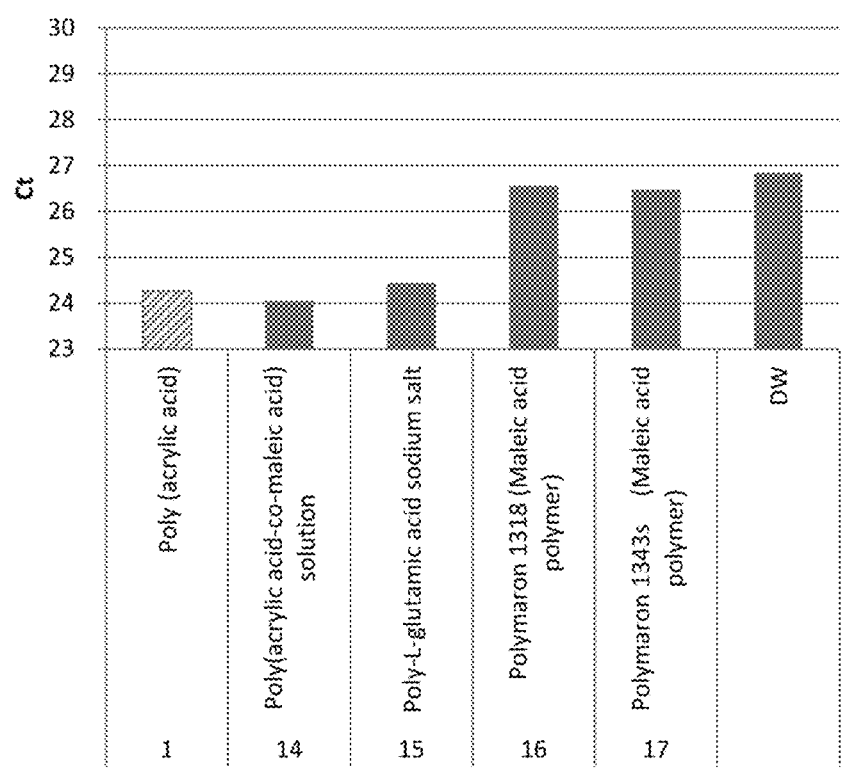
FIG. 3 Carrier effects of individual polymers 2.

Further, Ct values were obtained in the same manner using polymers which are negatively charged in aqueous solutions (Table 3, FIG. 3). All three polymers, i.e., polyanetholesulfonic acid sodium salt, poly(acrylic acid-co-maleic acid) solution and poly-L-glutamic acid sodium salt, each also having —COOH as a functional group, were rated +, revealing that they are effective as a carrier. Maleic acid polymers such as poly ethylene-co-ethyl acrylate-co-maleic anhydride and polymaron were rated ±, making it clear that even compounds with —COOH are weak in carrier effect when the —COOH is in the form of dicarboxy as in maleic acid.

TABLE 2

Carrier Effect of Each Polymer: 1

| | Polymer | $C_T$ | SD (N = 2) | side-chain | $\Delta C_T$ ($C_T - C_T$ without polymer) | Carrier effect |
|---|---|---|---|---|---|---|
| 1 | Poly (acrylic acid sodium salt) | 24.80 | 0.11 | —COOH | −1.89 | + |
| 2 | Gelatin | 26.45 | 0.02 | —NH$_2$, —COOH | −0.24 | ± |
| 3 | Carboxy methyl cellulose sodium salt | 25.36 | 0.12 | —CH$_2$COOH | −1.33 | + |
| 4 | Poly vinyl alcohol | 26.27 | 0.17 | —OH | −0.42 | ± |
| 5 | Poly ethylene imine | — | — | —NH$_2$ | — | − |
| 6 | Poly vinyl acetate | 26.54 | 0.06 | —COOCH$_3$ | −0.15 | ± |
| 7 | Poly ethylene glycole 20,000 | 26.90 | 0.53 | — | 0.21 | ± |
| 8 | Poly ethylene-co-ethyl acrylate-co-maleic anhydride | 26.79 | 0.24 | -maleic acid | 0.11 | ± |
| 9 | Poly vinyl pyrrolidone | 26.66 | 0.08 | -pyrrolidone | −0.03 | ± |
| 10 | Poly-L-lysine | 35.99 | 0.96 | —NH$_2$ | 9.30 | − |
| 11 | Poly phosphoric acid | 26.53 | 0.42 | —OPOO— | −0.16 | ± |
| 12 | Hydroxy ethyl cellulose | 27.42 | 1.34 | —CH$_2$CH$_2$OH | 0.74 | − |
| 13 | Dextran | 26.61 | 0.02 | — | −0.08 | ± |
| | DW (without carrier) | 26.69 | 0.10 | | | |
| | NTC | — | — | | | |

TABLE 3

Carrier Effect of Each Polymer: 2

| | Polymer | $C_T$ | SD (N = 3) | side-chain | $\Delta C_T$ ($C_T - C_T$ without polymer) | Carrier effect |
|---|---|---|---|---|---|---|
| 1 | Poly (acrylic acid) | 24.26 | 0.30 | —COOH | −1.58 | + |
| 14 | Poly(acrylic acid-co-maleic acid) solution | 24.04 | 0.05 | —COOH | −1.80 | + |
| 15 | Poly-L-glutamic acid sodium salt | 24.43 | 0.09 | —COOH | −1.41 | + |
| 16 | Polymaron 1318 (maleic acid polymer) | 26.56 | 0.13 | -maleic acid | −0.29 | ± |
| 17 | Polymaron 1343s (maleic acid polymer) | 26.48 | 0.02 | -maleic acid | −0.37 | ± |
| | DW (without carrier) | 26.85 | 0.23 | | | |
| | NTC | — | — | | | |

Example 3

Nucleic acid extraction was performed in two different steps with respect to the timing of carrier addition. Briefly, in one step (Original), PAAc was added to the reaction mixture immediately before binding of nucleic acid and support; and in another step (Carrier in sample), PAAc was directly added to the sample. The target gene was amplified by PCR (N=3). Sample preparation, nucleic acid extraction and PCR were performed in the same manner as described in Example 1 except for the timing of PAAc addition.

The results of PCR are shown in Table below. The Ct value was 25.03±0.14 in Original step but 26.79±0.04 when the carrier was added to the sample. Thus, PAAc did not exhibit any carrier effect in the latter step.

| | $C_T$ Mean | $C_T$ SD |
|---|---|---|
| Original | 25.03 | 0.14 |
| Carrier in Sample | 26.79 | 0.04 |

Example 4

In the composition of the reagent of the present invention, alcohol is required for binding nucleic acid to a support. Effect on the necessity of alcohol was examined using a carrier. As conditions under which a carrier exhibits its function of supporting the collection of nucleic acid, two steps were used. Briefly, in one step (Original), 2-propanol was contained in the binding buffer; and in another step (Binding buffer without 2-propanol), 2-propanol was not contained in the binding buffer. Nucleic acid extraction operations were performed in the above two steps separately, followed by amplification of the target gene by PCR (N=3). Sample preparation, nucleic acid extraction and PCR were performed in the same manner as described in Example 1 except for the presence/absence of 2-propanol.

The results of PCR are shown in Table below. The Ct value was 25.03±0.14 in the Original step but 31.91±0.31 when 2-propanol was not contained in the binding buffer. Thus, carrier effect was not exhibited in this step. It can be said that an alcohol must be contained in the binding buffer in order for the carrier to exhibit its effect.

|  | $C_T$ Mean | $C_T$ SD |
|---|---|---|
| Original | 25.03 | 0.14 |
| Binding buffer without 2-propanol | 31.91 | 0.31 |

All publications, patents and patent applications cited herein are incorporated herein by reference in their entirety.

INDUSTRIAL APPLICABILITY

According to the present invention, it is possible to improve the efficiency of nucleic acid collection in methods of nucleic acid collection using a support. The present invention is applicable to genetic examinations such as tests to identify viruses or pathogenic bacteria, detection of pathogenic microorganisms at an early stage of infection, survey of the source of infection, and diagnosis of leukemia or tumor at the genetic level.

SEQUENCE LISTING FREE TEXT

<SEQ ID NO. 1>
This shows the nucleotide sequence of Forward Primer M13KO7-F 4984.
5'-GCTATCAGTTCGCGCATTAAAGAC-3'

<SEQ ID NO. 2>
This shows the nucleotide sequence of Reverse Primer M13KO7-F 4984.
5'-GCTATCAGTTCGCGCATTAAAGAC-3'

The invention claimed is:

1. A method of extracting a nucleic acid from a sample, comprising:
    treating the sample comprising the nucleic acid with a solution comprising a chaotropic salt,
    adding an anionic polymer and
    mixing the resulting sample with a support and a solution comprising an alcohol,
    wherein the anionic polymer is at least one anionic polymer selected from the group consisting of polyanetholesulfonic add sodium salt, carboxymethyl cellulose salts, polyglutamic acid, polyglutamates, polyglutamic acid derivatives and copolymers comprising polyglutamic acid.

2. The method of claim 1, wherein the at least one alcohol is at least one selected from the group consisting of ethanol, isopropyl alcohol, n-propanol, n-butanol and 2-butanol.

3. The method claim 1, wherein the chaotropic salt is at least one chaotropic salt selected from the group consisting of guanidine hydrochloride, guanidine thiocyanate salt, guanidine thiocyanate, guanidine sulfate, guanidine isothiocyanate, isocyanate, sodium iodide, potassium iodide, urea, sodium bromide, potassium bromide, calcium bromide, ammonium bromide, sodium perchlorate, sodium thiocyanate, potassium thiocyanate, ammonium isothiocyanate, sodium chloride, potassium chloride and ammonium chloride.

4. The method of claim 1, wherein the support is a solid having a hydrophilic functional group in its surface layer.

5. The method of claim 4, wherein the hydrophilic functional group is at least one functional group selected from the group consisting of hydroxyl group, carboxyl group, carbonyl group, nitro group and silanol group.

6. The method of claim 4, wherein the support comprises magnetic particles.

7. The method of any one of claims 1 and 2 to 6, which is performed in an automated device.

8. The method of claim 6, further comprising capturing the support on the inner wall surface of a disposable chip with a magnet applied to the outer wall surface of the chip.

9. The method of claim 1, wherein the anionic polymer is at least one anionic polymer selected from the group consisting of carboxymethyl cellulose salts, polyanetholesulfonic acid salt, polyglutamates and polyglutamic acid derivatives.

* * * * *

```
                         SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Forward Primer M13KO7-F 4984

<400> SEQUENCE: 1
gctatcagtt cgcgcattaa agac                                           24

<210> SEQ ID NO 2
<211> LENGTH: 23
<212> TYPE: DNA
<213> ORGANISM: Artificial Sequence
<220> FEATURE:
<223> OTHER INFORMATION: Reverse Primer M13KO7-R 5110

<400> SEQUENCE: 2
cattggcaga ttcaccagtc aca                                            23
```